(12) United States Patent
Gall

(10) Patent No.: US 7,698,771 B2
(45) Date of Patent: Apr. 20, 2010

(54) ELECTRIC TOOTHBRUSH

(75) Inventor: Douglas A. Gall, Strongsville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1241 days.

(21) Appl. No.: 11/015,111

(22) Filed: Dec. 17, 2004

(65) Prior Publication Data

US 2005/0155167 A1 Jul. 21, 2005

Related U.S. Application Data

(60) Provisional application No. 60/531,071, filed on Dec. 19, 2003.

(51) Int. Cl.
*A61C 17/34* (2006.01)
(52) U.S. Cl. .............................. 15/22.1; 15/22.2; 15/28
(58) Field of Classification Search .................. 15/22.1, 15/22.2, 28
See application file for complete search history.

(56) References Cited

U.S. PATENT DOCUMENTS

| | | | |
|---|---|---|---|
| 793,587 A | 6/1905 | Johnson | |
| 1,212,001 A | 1/1917 | Baxter | |
| 1,255,028 A | 1/1918 | Leonard et al. | |
| 1,392,623 A | 10/1921 | Cheatham | |
| 1,517,320 A | 12/1924 | Stoddart | |
| 1,553,456 A | 9/1925 | Metrakos | |
| 1,557,244 A | 10/1925 | Dominque | |
| 1,896,731 A | 2/1933 | Lippett | |
| 1,981,688 A | 11/1934 | Conti | |
| 1,997,352 A | 4/1935 | Fleet | |
| 2,044,863 A | 6/1936 | Sticht | |
| 2,140,307 A | 12/1938 | Belaschk et al. | |
| 2,172,624 A | 9/1939 | Robert | |
| 2,215,031 A | 9/1940 | Elmore | |
| 2,379,049 A | 6/1945 | Tompkins | |
| 2,435,421 A | 2/1948 | Blair | |
| 2,601,567 A | 6/1952 | Steinberg | |
| 3,115,652 A | 12/1963 | Zerbee | |
| 3,129,449 A | 4/1964 | Cyzer | |
| 3,159,859 A | 12/1964 | Rasmussen | |

(Continued)

FOREIGN PATENT DOCUMENTS

CN 2271352 7/1996

(Continued)

OTHER PUBLICATIONS

Office Action for U. S. Appl. No. 11/295,907; P&G Case 9853; dated Jun. 5, 2009.

(Continued)

*Primary Examiner*—Randall Chin
(74) *Attorney, Agent, or Firm*—Vladimir Vitenberg; George H. Leal; David M. Weirich

(57) ABSTRACT

An electric toothbrush is disclosed. The electric toothbrush includes a body having an interior hollow region for retaining one or more motors, batteries, and drive mechanisms. The toothbrush includes one or more bristle carriers. Each of the bristle carriers undergoes some type of movement and is driven by the one or more motors and drive mechanisms. Various combinations of movement of the bristle carriers are described. And, numerous drive train mechanisms are disclosed for achieving the noted motions.

4 Claims, 9 Drawing Sheets

U.S. PATENT DOCUMENTS

| | | |
|---|---|---|
| 3,160,902 A | 12/1964 | Aymar |
| 3,178,754 A | 4/1965 | Cleverdon |
| 3,195,537 A | 7/1965 | Blasi |
| 3,242,516 A | 3/1966 | Cantor |
| 3,379,906 A | 4/1968 | Spohr |
| 3,398,421 A | 8/1968 | Rashbaum |
| 3,509,874 A | 5/1970 | Stillman |
| 3,524,088 A | 8/1970 | Ryckman |
| 3,538,530 A | 11/1970 | Stemme |
| 3,588,936 A | 6/1971 | Duve |
| 3,592,188 A | 9/1971 | Barnett |
| 3,935,869 A | 2/1976 | Reinsch |
| 3,945,076 A | 3/1976 | Sung |
| 3,978,852 A | 9/1976 | Annoni |
| 4,027,348 A | 6/1977 | Flowers et al. |
| 4,156,620 A | 5/1979 | Clemens |
| 4,175,299 A | 11/1979 | Teague, Jr. et al. |
| 4,274,173 A | 6/1981 | Cohen |
| 4,326,314 A | 4/1982 | Moret et al. |
| 4,346,492 A | 8/1982 | Solow |
| 4,397,055 A | 8/1983 | Cuchiara |
| 4,545,087 A | 10/1985 | Nahum |
| 4,791,945 A | 12/1988 | Moriyama |
| 4,795,347 A | 1/1989 | Maurer |
| 4,845,795 A | 7/1989 | Crawford et al. |
| 4,974,278 A | 12/1990 | Hommann |
| 4,989,287 A | 2/1991 | Scherer |
| 4,995,131 A | 2/1991 | Takeda |
| 5,033,150 A | 7/1991 | Gross et al. |
| 5,068,939 A | 12/1991 | Holland |
| 5,070,567 A | 12/1991 | Holland |
| 5,077,855 A | 1/1992 | Ambasz |
| 5,088,145 A | 2/1992 | Whitefield |
| 5,120,225 A | 6/1992 | Amit |
| 5,138,734 A | 8/1992 | Chung |
| 5,170,525 A | 12/1992 | Cafaro |
| 5,186,627 A | 2/1993 | Amit et al. |
| 5,226,206 A | 7/1993 | Davidovitz et al. |
| 5,253,382 A | 10/1993 | Beny |
| 5,259,083 A | 11/1993 | Stansbury, Jr. |
| 5,276,932 A | 1/1994 | Byrd |
| 5,301,381 A | 4/1994 | Klupt |
| 5,311,633 A | 5/1994 | Herzog et al. |
| 5,321,866 A | 6/1994 | Klupt |
| 5,353,460 A | 10/1994 | Bauman |
| 5,359,747 A | 11/1994 | Amakasu |
| 5,383,242 A | 1/1995 | Bigler et al. |
| 5,398,366 A | 3/1995 | Bradley |
| 5,404,608 A | 4/1995 | Hommann |
| 5,416,942 A | 5/1995 | Baldacci et al. |
| 5,448,792 A | 9/1995 | Wiedemann et al. |
| 5,465,444 A | 11/1995 | Bigler et al. |
| 5,493,747 A | 2/1996 | Inakagata et al. |
| 5,504,958 A | 4/1996 | Herzog |
| 5,504,959 A | 4/1996 | Yukawa et al. |
| 5,524,312 A | 6/1996 | Tan |
| 5,528,786 A | 6/1996 | Porat et al. |
| 5,577,285 A | 11/1996 | Drossler |
| 5,617,601 A | 4/1997 | McDougall |
| 5,617,603 A | 4/1997 | Mei |
| 5,625,916 A | 5/1997 | McDougall |
| 5,679,991 A | 10/1997 | Wolf |
| 5,687,442 A | 11/1997 | McLain |
| 5,727,273 A | 3/1998 | Pai |
| 5,732,432 A | 3/1998 | Hui |
| 5,732,433 A | 3/1998 | Droessler et al. |
| 5,738,575 A | 4/1998 | Bock |
| 5,778,474 A | 7/1998 | Shek |
| 5,784,743 A | 7/1998 | Shek |
| RE35,941 E | 11/1998 | Stansbury, Jr. |
| 5,836,030 A | 11/1998 | Hazeu et al. |
| 5,842,244 A | 12/1998 | Hilfinger |
| 5,842,245 A | 12/1998 | Pai |
| 5,850,655 A | 12/1998 | Gocking et al. |
| 5,862,558 A | 1/1999 | Hilfinger et al. |
| 5,867,856 A | 2/1999 | Herzog |
| 5,956,797 A | 9/1999 | Wilson |
| 5,974,613 A | 11/1999 | Herzog |
| 5,974,615 A | 11/1999 | Schwarz-Hartmann et al. |
| 6,000,083 A | 12/1999 | Blaustein et al. |
| 6,106,290 A | 8/2000 | Weissman |
| 6,138,310 A | 10/2000 | Porper et al. |
| 6,178,579 B1 | 1/2001 | Blaustein et al. |
| 6,189,693 B1 | 2/2001 | Blaustein et al. |
| 6,195,828 B1 | 3/2001 | Fritsch |
| 6,237,178 B1 | 5/2001 | Krammer et al. |
| 6,308,359 B2 | 10/2001 | Fritsch et al. |
| 6,311,837 B1 | 11/2001 | Blaustein et al. |
| 6,347,425 B1 | 2/2002 | Fattori et al. |
| 6,360,395 B2 | 3/2002 | Blaustein et al. |
| 6,371,294 B1 | 4/2002 | Blaustein et al. |
| 6,421,865 B1 | 7/2002 | McDougall |
| 6,421,866 B1 | 7/2002 | McDougall |
| 6,434,773 B1 | 8/2002 | Youti |
| 6,446,294 B1 | 9/2002 | Specht |
| 6,453,498 B1 | 9/2002 | Wu |
| 6,463,615 B1 | 10/2002 | Gruber et al. |
| 6,510,575 B2 | 1/2003 | Calabrese |
| 6,536,066 B2 | 3/2003 | Dickie |
| 6,546,585 B1 | 4/2003 | Blaustein et al. |
| 6,564,940 B2 | 5/2003 | Blaustein et al. |
| 6,574,820 B1 | 6/2003 | DePuydt et al. |
| 6,623,698 B2 | 9/2003 | Cox et al. |
| 0,182,746 A1 | 10/2003 | Fattori, et al. |
| 6,725,490 B2 | 4/2004 | Blaustein et al. |
| 6,751,823 B2 | 6/2004 | Biro et al. |
| 6,760,946 B2 | 7/2004 | DePuydt |
| 6,836,917 B2 | 1/2005 | Blaustein et al. |
| 6,889,401 B2 | 5/2005 | Fattori et al. |
| 6,892,412 B2 | 5/2005 | Gatzemeyer et al. |
| 6,892,413 B2 | 5/2005 | Blaustein et al. |
| 6,928,685 B1 | 8/2005 | Blaustein et al. |
| 6,932,216 B2 | 8/2005 | Blaustein et al. |
| 6,944,901 B2 | 9/2005 | Gatzemeyer et al. |
| 6,952,854 B2 | 10/2005 | Blaustein et al. |
| 6,966,093 B2 | 11/2005 | Eliav et al. |
| 6,983,507 B2 | 1/2006 | McDougall |
| 7,124,461 B2 | 10/2006 | Blaustein et al. |
| 7,137,163 B2 | 11/2006 | Gatzemeyer et al. |
| 7,140,058 B2 | 11/2006 | Gatzemeyer et al. |
| 7,140,059 B2 | 11/2006 | Scherl |
| 7,150,061 B2 | 12/2006 | Kwong |
| 7,162,764 B2 | 1/2007 | Drossler et al. |
| 7,225,494 B2 | 6/2007 | Chan et al. |
| 7,258,747 B2 | 8/2007 | Vago et al. |
| 7,302,726 B2 | 12/2007 | Braun |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan et al. |
| 7,430,777 B2 | 10/2008 | Scherl |
| 7,430,778 B2 | 10/2008 | Gatzemeyer et al. |
| 7,451,514 B2 | 11/2008 | Blaustein, et al. |
| 7,520,016 B2 | 4/2009 | Kressner |
| 7,552,497 B2 | 6/2009 | Gatzemeyer et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0059685 A1 | 5/2002 | Paffrath |
| 2002/0078514 A1 | 6/2002 | Blaustein et al. |
| 2002/0138926 A1 | 10/2002 | Brown et al. |
| 2002/0152564 A1 | 10/2002 | Blaustein et al. |

| | | | |
|---|---|---|---|
| 2003/0066145 A1 | 4/2003 | Prineppi | |
| 2003/0074751 A1 | 4/2003 | Wu | |
| 2003/0084525 A1 | 5/2003 | Blaustein et al. | |
| 2003/0084526 A1 | 5/2003 | Brown et al. | |
| 2003/0084527 A1 | 5/2003 | Brown et al. | |
| 2003/0140435 A1 | 7/2003 | Eliav et al. | |
| 2003/0140437 A1 | 7/2003 | Eliav et al. | |
| 2003/0154567 A1 | 8/2003 | Drossler et al. | |
| 2003/0163881 A1 | 9/2003 | Driesen et al. | |
| 2003/0163882 A1 | 9/2003 | Blaustein et al. | |
| 2003/0196283 A1 | 10/2003 | Eliav et al. | |
| 2003/0213075 A1 | 11/2003 | Hui et al. | |
| 2003/0226223 A1 | 12/2003 | Chan et al. | |
| 2004/0045105 A1 | 3/2004 | Eliav et al. | |
| 2004/0060137 A1 | 4/2004 | Eliav et al. | |
| 2004/0074026 A1 | 4/2004 | Blaustein et al. | |
| 2004/0083566 A1 | 5/2004 | Blaustein | |
| 2004/0088807 A1 | 5/2004 | Blaustein et al. | |
| 2004/0143917 A1 | 7/2004 | Ek | |
| 2004/0168272 A1 | 9/2004 | Prineppi | |
| 2004/0177458 A1 | 9/2004 | Chan et al. | |
| 2004/0177462 A1 | 9/2004 | Brown, Jr. | |
| 2005/0000043 A1 | 1/2005 | Chan et al. | |
| 2005/0000045 A1 | 1/2005 | Blaustein | |
| 2005/0091771 A1 | 5/2005 | Blaustein et al. | |
| 2005/0102776 A1* | 5/2005 | Mathur | 15/22.1 |
| 2005/0155167 A1 | 7/2005 | Gall | |
| 2005/0268409 A1 | 12/2005 | Blaustein et al. | |
| 2005/0279974 A1 | 12/2005 | Blaustein et al. | |
| 2006/0032006 A1 | 2/2006 | Gall | |
| 2006/0048314 A1 | 3/2006 | Kressner | |
| 2006/0048315 A1 | 3/2006 | Chan et al. | |
| 2006/0137118 A1 | 6/2006 | Blaustein | |
| 2006/0254006 A1 | 11/2006 | Blaustein et al. | |
| 2006/0254007 A1 | 11/2006 | Banning | |
| 2007/0251033 A1 | 11/2007 | Gall | |
| 2008/0010761 A1 | 1/2008 | Blaustein et al. | |
| 2008/0016633 A1 | 1/2008 | Blaustein et al. | |
| 2008/0078040 A1 | 4/2008 | Braun | |
| 2009/0106923 A1 | 4/2009 | Boland | |

FOREIGN PATENT DOCUMENTS

| | | |
|---|---|---|
| CN | 2236827 Y | 10/1996 |
| CN | 2271353 | 10/1996 |
| CN | 2274947 Y | 2/1998 |
| CN | 1187341 A | 7/1998 |
| CN | 2324987 | 6/1999 |
| CN | 2324988 | 6/1999 |
| CN | 2681701 Y | 3/2005 |
| DE | 3406112 | 8/1985 |
| DE | 3544256 | 8/1987 |
| DE | 4003305 | 8/1991 |
| DE | 29600236 | 4/1996 |
| DE | 29613608 | 11/1996 |
| DE | 29618755 | 3/1997 |
| DE | 19701964 | 7/1998 |
| DE | 298 09 977 | 2/1999 |
| DE | 19802904 | 7/1999 |
| DE | 19803311 | 8/1999 |
| EP | 259648 | 3/1988 |
| EP | 1053721 | 11/2000 |
| EP | 1059049 | 12/2000 |
| GB | 2247297 | 2/1992 |
| GB | 2290224 | 12/1995 |
| GB | 2319170 | 5/1998 |
| GB | 2 365 759 A | 2/2002 |
| JP | 40-8743 | 8/1965 |
| JP | 57-89810 | 6/1982 |
| JP | 2-19241 | 2/1990 |
| JP | 02-218309 | 8/1990 |
| JP | 05-146313 | 6/1993 |
| JP | 05-146314 | 6/1993 |
| JP | 7-116020 | 5/1995 |
| JP | 7-116021 | 5/1995 |
| JP | 7-116023 | 5/1995 |
| JP | 07-116024 | 5/1995 |
| JP | 7-93892 | 10/1995 |
| JP | 8-322641 | 10/1996 |
| JP | 10-066704 | 3/1998 |
| JP | 2804940 | 7/1998 |
| JP | 11253233 A | 9/1999 |
| KR | 1984-0004668 | 9/1984 |
| KR | 1986-0001137 | 6/1986 |
| KR | 1994-0013418 | 7/1994 |
| KR | 1995-0002814 | 2/1995 |
| KR | 1995-00108 | 5/1995 |
| KR | 1997-0000408 | 1/1997 |
| KR | 1997-0000409 | 1/1997 |
| KR | 1995-0024551 | 4/1998 |
| KR | 143460 | 4/1998 |
| WO | WO 02/102187 A1 | 12/2002 |
| WO | WO 2004/045448 A1 | 6/2004 |

OTHER PUBLICATIONS

U. S. Appl. No. 10/237,902, Filed Sep. 09, 2002 entitled Topper for Power Toothbrush and Method for Forming the Same, all pages.
Office Action for U. S. Appl. No. 10/903,222; P&G Case 8777C; dated Apr. 11, 2005.
Office Action for U. S. Appl. No. 10/903,222; P&G Case 8777C; dated Oct. 19, 2004.
Office Action for U. S. Appl. No. 11/200,680; P&G Case 8777CC; dated Sep. 22, 2005.
Office Action for U. S. Appl. No. 11/358,582; P&G Case 8777CCC; dated Mar. 17, 2008.
Office Action for U. S. Appl. No. 11/358,582; P&G Case 8777CCC; dated Apr. 14, 2006.
Office Action for U. S. Appl. No. 11/358,582; P&G Case 8777CCC; dated Apr. 17, 2007.
Action for U. S. Appl. No. 11/358,582; P&G Case 8777CCC; dated Jun. 9, 2008.
Advisory Action for U. S. Appl. No. 11/358,582; P&G Case 8777CCC; dated Jul. 27, 2007.
Office Action for U. S. Appl. No. 11/358,582; P&G Case 8777CCC; dated Sep. 5, 2008.
Office Action for U. S. Appl. No. 11/358,582; P&G Case 8777CCC; dated Sep. 6, 2007.
Office Action for U. S. Appl. No. 11/358,582; P&G Case 8777CCC; dated Sep. 29, 2006.
Office Action for U. S. Appl. No. 10/676,955; P&G Case 8778CC; dated Jan. 24, 2005.
Office Action for U. S. Appl. No. 10/676,955; P&G Case 8778CC; dated Jan. 24, 2005.
Office Action for U. S. Appl. No. 10/676,955; P&G Case 8778CC; dated Jul. 12, 2005.
Office Action for U. S. Appl. No. 10/676,955; P&G Case 8778CC; dated Jul. 29, 2004.
Office Action for U. S. Appl. No. 10/927,845; P&G Case 8778CCC2; dated Dec. 28, 2004.
Office Action for U. S. Appl. No. 10/929,288; P&G Case 8778CCC3; dated Mar. 18, 2005.
Office Action for U. S. Appl. No. 10/929,288; P&G Case 8778CCC3; dated Aug. 24, 2005.
Office Action for U. S. Appl. No. 11/514,742; P&G Case 8778CCC3C; dated Mar. 17, 2008.
Office Action for U. S. Appl. No. 11/514,742; P&G Case 8778CCC3C; dated Aug. 17, 2007.
Office Action for U. S. Appl. No. 11/514,742; P&G Case 8778CCC3C; dated Apr. 10, 2008.
Office Action for U. S. Appl. No. 11/006,972; P&G Case 8778CCC4; dated Mar. 24, 2005.
Office Action for U. S. Appl. No. 10/896,540; P&G Case 8778CCC; dated Oct. 4, 2004.
Office Action for U. S. Appl. No. 11/414,908; P&G Case 8829RRCC; dated May 23, 2007.

Office Action for U. S. Appl. No. 11/801,000; P&G Case 8829RRCCC; dated Jun. 20, 2008.
Office Action for U. S. Appl. No. 11/801,000; P&G Case 8829RRCCC; dated Sep. 26, 2008.
Office Action for U .S. Appl. No. 11/801,000; P&G Case 8829RRCCC; dated Oct. 26, 2007.
Office Action for U. S. Appl. No. 11/801,000; P&G Case 8829RRCCC; dated Dec. 5, 2008.
Office Action for U. S. Appl. No. 10/308,959; P&G Case 8880R; dated Feb. 16, 2006.
Advisory Action for U. S. Appl. No. 11/486,725; P&G Case 8880RC; dated Jan. 28, 2008.
Office Action for U. S. Appl. No. 11/486,725; P&G Case 8880RC; dated Jan. 28, 2009.
Office Action for U. S. Appl. No. 11/486,725; P&G Case 8880RC; dated Jan. 29, 2007.
Office Action for U. S. Appl. No. 11/486,725; P&G Case 8880RC; dated Apr. 10, 2008.
Office Action for U. S. Appl. No. 11/486,725; P&G Case 8880RC; dated Aug. 13, 2007.
Office Action for U. S. Appl. No. 11/893,469; P&G Case 8880RCC; dated Oct. 14, 2008.
Office Action for U. S. Appl. No. 11/893,469; P&G Case 8880RCC; dated Dec. 18, 2008.
Office Action for U. S. Appl. No. 11/410,808; P&G Case 9186C; dated Feb. 15, 2007.
Office Action for U. S. Appl. No. 11/410,808; P&G Case 9186C; dated Jul. 17, 2007.
Office Action for U. S. Appl. No. 11/220,219; P&G Case 9770; dated Oct. 20, 2008.
Office Action for U. S. Appl. No. 10/367,373; dated Mar. 9, 2004.
Office Action for U. S. Appl. No. 09/425,423; P&G Case Z-3735; dated Jan. 31, 2002.
Office Action for U. S. Appl. No. 09/425,423; P&G Case Z-3735; dated Aug. 14, 2002.
Office Action for U. S. Appl. No. 10/331,799; P&G Case Z-3557; dated Apr. 19, 2005.
Office Action for U. S. Appl. No. 10/331,799; P&G Case Z-3557; dated Oct. 14, 2005.
Office Action for U. S. Appl. No. 10/331,799; P&G Case Z-3557; dated Feb. 23, 2006.
Office Action for U. S. Appl. No. 09/993,167; P&G Case 8778; dated Dec. 18, 2002.
Office Action for U. S. Appl. No. 09/993,167; P&G Case 8778; dated Apr. 16, 2003.

* cited by examiner

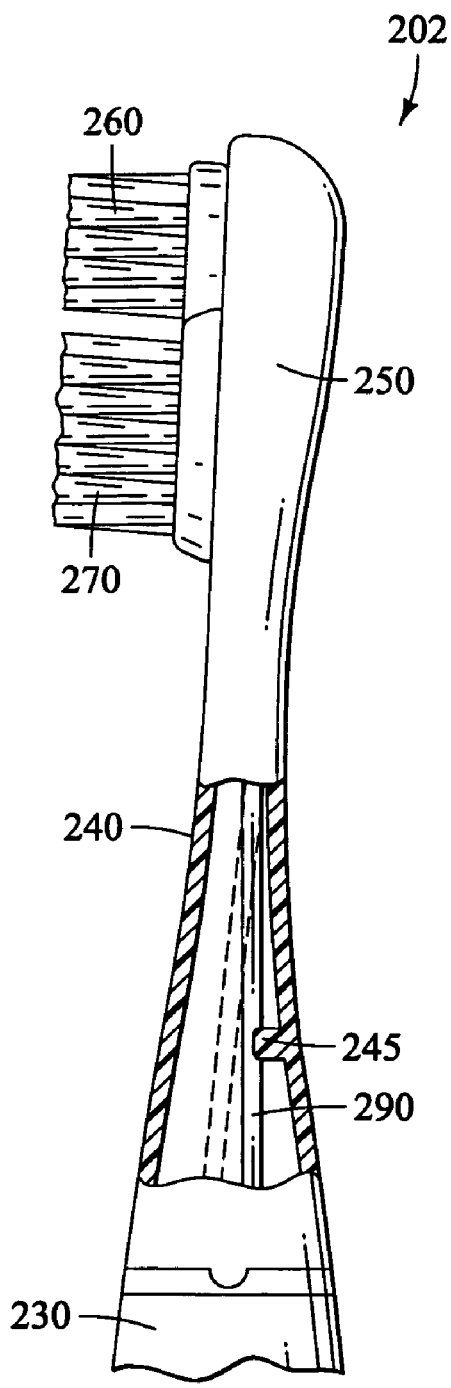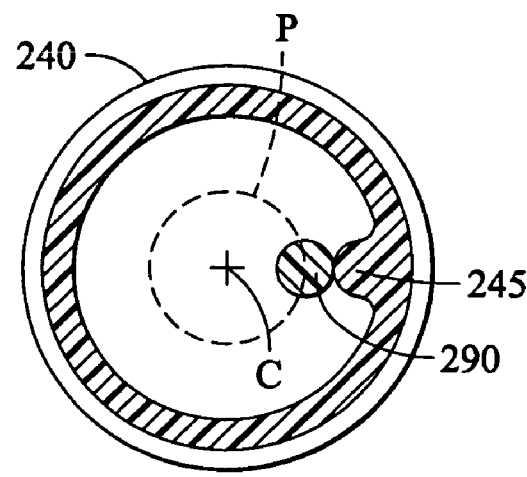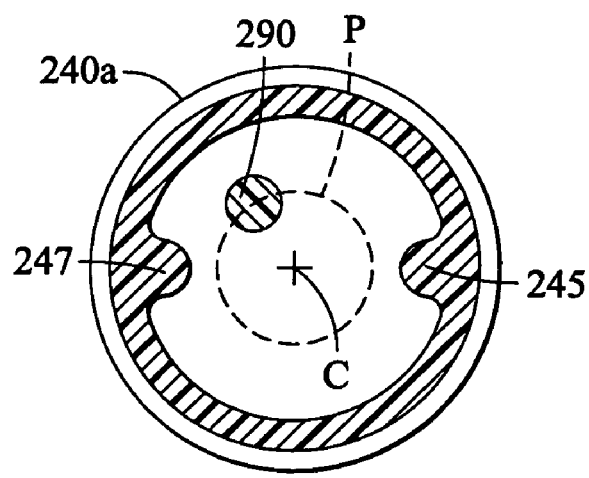
FIG. 14
FIG. 15
FIG. 16

ELECTRIC TOOTHBRUSH

CROSS REFERENCE TO RELATED APPLICATION

This application claims priority of U.S. provisional application Ser. No. 60/531,071 filed Dec. 19, 2003 is herein incorporated by reference.

FIELD OF THE INVENTION

The present invention relates to the field of toothbrushes, and more particularly, the invention relates to the field of electrically powered toothbrushes.

BACKGROUND OF THE INVENTION

Most known electric toothbrushes utilize a single bristle carrier that is powered or otherwise driven by an electric motor incorporated in the toothbrush. The bristle carriers in these toothbrushes undergo a wide array of motions. For example, bristle carriers that undergo rotary motion are well known. Bristle carriers that move back and forth in a linear fashion within the plane of the brush are also known. And, bristle carriers that move in a linear fashion perpendicular to the plane of the brush are also known such as in U.S. Pat. No. 5,974,615. Although satisfactory in certain respects, a need still exists for an improved powered toothbrush design.

Numerous attempts have been made to improve the design, efficiency, cleaning efficacy, simplicity, and/or commercial viability of electric toothbrushes. One approach has been the provision of multiple powered bristle carriers. Most artisans have grouped multiple sets of bristles along an end of a brush and incorporated a drive mechanism for simultaneously rotating each of the bristle sets, together. Exemplary designs include those disclosed in U.S. Pat. Nos. 3,242,516; 4,156,620; 4,845,795; 5,088,145; 5,020,179; 4,827,550; and 4,545,087, all of which are hereby incorporated by reference.

Although bristle carriers that undergo various combinations of movement have been disclosed in the prior art, there remains a need to provide an electric toothbrush with one or more bristle carriers that provides additional combinations of motion.

SUMMARY OF THE INVENTION

The present invention provides, in a first aspect, an electric toothbrush comprising an elongate handle having a motor disposed therein, and a head having a longitudinal axis and a movable bristle carrier, wherein the head is stationary during use. That is, the head is stationary with respect to the handle or main body portion of the toothbrush. The electric toothbrush also comprises a neck extending between the handle and the head. The toothbrush further comprises a shaft directly coupled to the moveable bristle carrier and operatively connected to the motor. Movement of the shaft causes the movable bristle carrier to oscillate about an axis generally perpendicular to the longitudinal axis of the head and to additionally reciprocate along the axis generally perpendicular to the longitudinal axis of the head. The movable bristle carrier further comprises a ramp disposed on an underside surface of the carrier. Additionally, a post is provided within the interior portion of the head. The post is positioned and configured such that the ramp and the post slidingly engage each other during operation of the toothbrush to thereby result in reciprocation of the bristle carrier.

In yet another aspect, the present invention provides an electric toothbrush comprising an elongate handle having a longitudinal axis and a motor disposed therein. The electric toothbrush also comprises a moveable head having a second longitudinal axis and a movable bristle carrier. The movable head is movable relative to the handle. The electric toothbrush further comprises a movable neck extending between the handle and the head. And, the electric toothbrush comprises a shaft operatively coupled to the motor and to the movable bristle carrier. The shaft operatively engages the movable neck such that movement of the shaft causes the movable bristle carrier to oscillate about an axis generally perpendicular to the second longitudinal axis of the head. Movement of the shaft also causes the moveable neck and the moveable head to move in a direction generally transverse to the longitudinal axis of the handle.

In yet another aspect, the present invention provides an electric toothbrush comprising an elongate handle having a longitudinal axis and a motor disposed therein. The electric toothbrush further comprises a movable head having a second longitudinal axis and a movable bristle carrier wherein the movable head is movable relative to the handle. The electric toothbrush further comprises a movable neck extending between the handle and the head. And, the electric toothbrush comprises a shaft operatively coupled to the motor and to the movable bristle carrier. The shaft operatively engages the movable neck such that the motor imparts only a single motion to the shaft and wherein movement of the shaft causes the movable bristle carrier to oscillate about an axis generally perpendicular to the second longitudinal axis of the head. Furthermore, movement of the shaft causes the movable neck and the movable head to move in a direction generally transverse to the longitudinal axis of the handle.

In yet another aspect, the present invention provides an electric toothbrush comprising an elongate handle having a longitudinal axis and a motor disposed therein. The toothbrush further comprises a movable head having a second longitudinal axis and a movable bristle carrier. The head is movable relative to the handle. The toothbrush further comprises a movable neck extending between the handle and the head. And, the electric toothbrush comprises a shaft operatively coupled to the motor and to the movable bristle carrier wherein the shaft operatively engages the movable neck. Movement of the shaft causes the movable bristle carrier to oscillate about an axis generally perpendicular to the second longitudinal axis of the head. Additionally, movement of the shaft causes the moveable neck and the movable head to move in a direction generally transverse to the longitudinal axis of the handle about a pivot point at an end of the neck proximate the handle.

In yet another aspect, the present invention provides an electric toothbrush comprising an elongate handle having a longitudinal axis and a motor disposed therein. The electric toothbrush further comprises a movable head having a second longitudinal axis and a movable bristle carrier, wherein the movable head is movable relative to the handle. The electric toothbrush further comprises a movable neck extending between the handle and the head. And, the electric toothbrush comprises a shaft operatively coupled to the motor and to the movable bristle carrier such that the shaft repetitively engages and disengages the movable neck. Movement of the shaft causes the movable bristle carrier to oscillate about an axis generally perpendicular to the second longitudinal axis of the head and wherein the repetitive engagement and disengagement of the shaft causes the movable neck and the movable head to move in a direction generally transverse to the longitudinal axis of the handle.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which:

FIG. 14 is a partial fragmentary side view of yet another preferred embodiment toothbrush utilizing an orbital motion drive shaft in accordance with the present invention.

FIG. 15 is a view of the underside of the neck and head portion of the toothbrush depicted in FIG. 14.

FIG. 16 is a view of the underside of the head and neck portion of a variant version of the toothbrush depicted in FIG. 14.

DETAILED DESCRIPTION OF THE PREFERRED EMBODIMENTS

As will be appreciated, the present invention is directed to electric toothbrushes, including electric toothbrushes having replaceable brush head ends, replaceable bristle carriers and electric toothbrushes having one or more bristle carriers. In particular, the present invention is directed to an electric toothbrush with two bristle carriers, each of which is driven by an electric motor incorporated within the toothbrush body.

Specifically, the present invention can be used in conjunction with electric toothbrushes, brush heads, and bristle carriers that include shafts that rotate, oscillate, orbit, or reciprocate (as well as combinations thereof) to impart motion to the first and second bristle carriers. In addition, the present invention can be used in combination with electric toothbrushes, brush heads, and bristle carriers where the shaft is operatively connected to both the first and second bristle carriers or only one of the bristle carriers. In the latter instance, the bristle carriers are themselves interconnected so that a motion is imparted to the bristle carrier that is not directly coupled to the shaft.

Before describing the various preferred embodiment toothbrushes, it is instructive to define the various types of motions referenced herein. As used herein, the term "angular motion" refers to any angular displacement. "Linear motion" is movement along a straight or substantially straight, line or direction. "Primarily linear motion" is described below. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion (i.e., motion that extends through 360 degrees or more) that is substantially in the form of a circle is referred to as rotary motion. Periodic angular motion is motion that extends through less than 360 degrees and is referred to as oscillating motion. Curvilinear motions can also be either constant (i.e., unidirectional) or periodic (i.e., reverses direction). Periodic linear motion is referred to as "reciprocation". Orbital motion is generally rotary motion of a body about a point that is different than the center point of the body.

Figure 1:
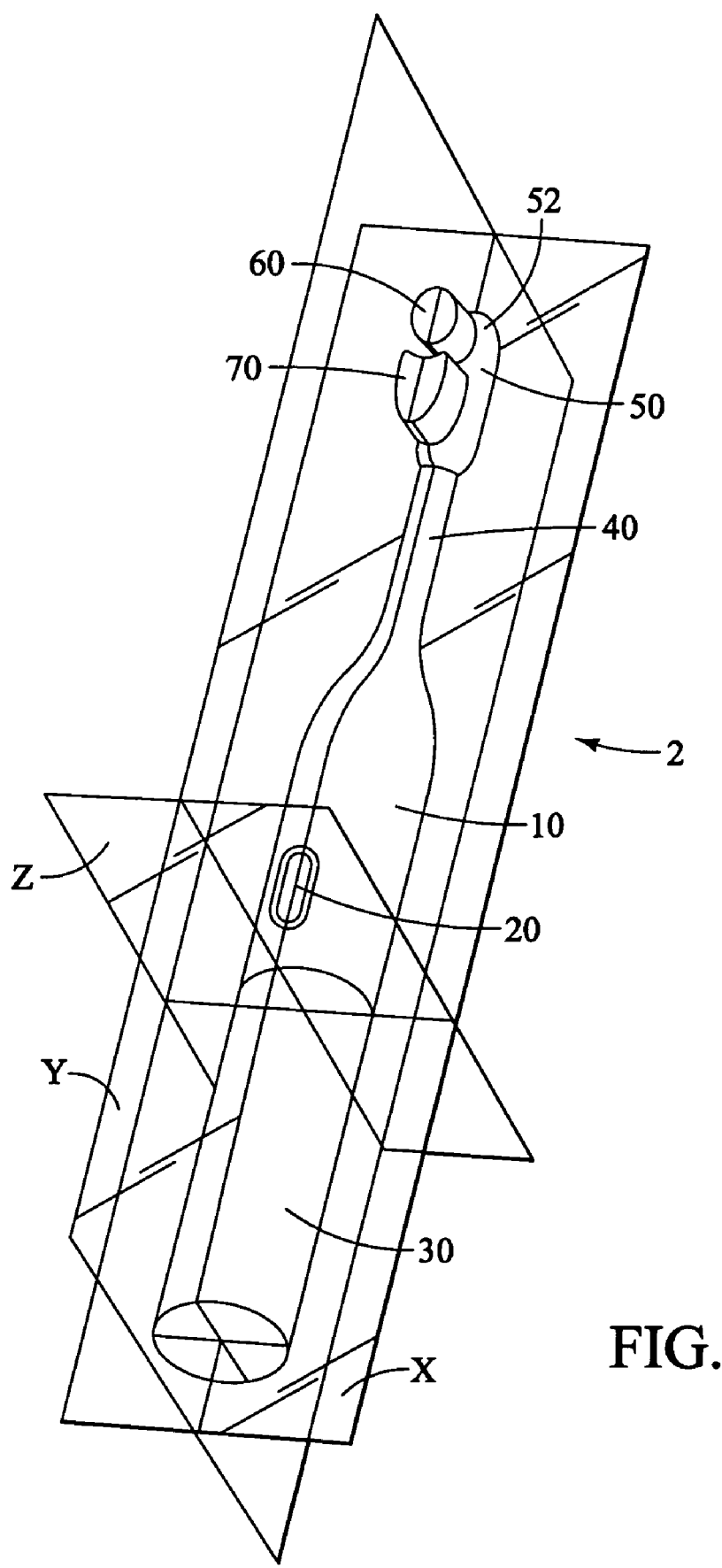
FIG. 1 is a perspective view of a preferred embodiment toothbrush in accordance with the present invention illustrating various planes and their orientation with respect to the toothbrush.

The above-described motions can also occur along one or more axes of a bristle carrier. Accordingly, motion is described herein as being either one, two, or three dimensional motion depending upon the number of axial coordinates required to describe the position of a bristle carrier during its movement. The axes, X, Y, and Z, are shown in FIG. 1. One dimensional motion is motion that can be described by a single coordinate (e.g., X, Y, or Z coordinates). Typically, only linear motion can be one dimensional. For example, periodic linear motion substantially along only the Y axis is one dimensional motion (referred to herein as a "pulsing motion"). Two dimensional motion is movement by a bristle carrier that requires two coordinates (e.g., X and Y coordinates) to describe the path of travel of the bristle carrier. Angular motion that occurs in a single plane is two dimensional motion. Three dimensional motion is movement by a bristle carrier that requires three coordinates (e.g., X, Y, and Z coordinates) to describe the path of travel of the bristle carrier. An example of three dimensional motion is movement by a bristle carrier in the path of a helix.

FIG. 1 is a perspective view of a preferred embodiment toothbrush 2 in accordance with the present invention. The toothbrush 2 comprises an elongated body 10 having a handle 30, a head 50, and a neck 40 extending between the handle 30 and the head 50. A switch 20 is provided or made accessible along the outer region of the body 10. As will be appreciated, the switch 20 actuates an electrical motor contained within the body 10 of toothbrush 2. The motor (not shown) and a drive mechanism as described herein (not shown) provide a powered drive for one or more bristle carriers disposed near a distal end of the toothbrush. Specifically, the toothbrush 2 further includes a first bristle carrier 60 and a second bristle carrier 70. The first carrier 60 is located adjacent a distal-most end 52 of the head 50. As described in greater detail herein, upon activation of the drive mechanism, the first and second bristle carriers undergo a particular combination of motions. The motions are best described in terms of the axes X, Y, and Z and the planes which contain these axes. As referenced herein, these planes are referred to as the X plane, Y plane, or Z plane.

The X axis is generally referred to herein as the longitudinal axis and generally extends along a longitudinal or lengthwise dimension (as seen from the top planar view of the toothbrush) of the toothbrush head or the bristle carrier. The longitudinal axis of the toothbrush head or bristle carrier may coincide with the longitudinal axes of the toothbrush neck and/or handle, although it need not do so as for example where the toothbrush head is angled with respect to either the toothbrush neck or handle. In certain embodiments described herein, the head and/or neck component may have a different longitudinal axis than the longitudinal axis of the handle. In this instance, the longitudinal axis of the handle can be referred to as a first longitudinal axis and that of the head and/or neck, referred to as a second longitudinal axis. The Y axis is transverse to the X axis and generally bisects the toothbrush head into its left and right halves. The Z axis is orthogonal or perpendicular to the X and Y axes.

Plane X contains the X axis and is generally referred to herein as the plane of the toothbrush or the plane of the toothbrush head. This plane generally extends along the longitudinal dimension of the toothbrush or the toothbrush head. The Y plane contains the Y axis and extends through the toothbrush and is perpendicular to the X plane. The Y plane either bisects the toothbrush or is parallel to a plane that does. The Z plane is perpendicular to both the X plane and the Y plane.

Furthermore, it is useful to address the terminology used in describing the preferred embodiment toothbrushes and bristle carriers. As used herein, the term "forward" refers to the direction from the handle to the head while the term "rearward" refers to the direction from the head to the handle. A longitudinal direction is a direction that generally corresponds to a longitudinal or X axis but which may not lie in the same plane as the axis. For example, the longitudinal axes of a shaft and a bristle carrier may not extend in the same plane but generally extend in the same direction from a top planar view. Similarly, a neck and head that are angled with respect to each other may not have longitudinal axes that extend in the same plane, but do have axes which extend in the same general longitudinal direction from a top planar view. Many of the preferred embodiment electric toothbrushes typically have an elongated head with a longitudinal axis passing through the longest dimension thereof. This axis typically extends in the same general direction as the longitudinal axes of the toothbrush neck and/or shaft. This axis is generally referred to as the longitudinal axis of the toothbrush. By the phrase "same general direction," some angular deviation is contemplated between the axes. Various references are also made herein to the "plane of the toothbrush." As will be understood, this is generally the plane within which extends the longitudinal axis of the toothbrush head.

And, as described herein, the first bristle carrier is the bristle carrier that is located at the distal-most end of the toothbrush. The second bristle carrier is the next bristle carrier positioned alongside or proximate to the first bristle carrier and rearward therefrom. A third bristle carrier is proximate the second bristle carrier and is positioned rearward of the second bristle carrier. A fourth bristle carrier is rearward of the third and so on.

Generally, the preferred embodiment toothbrushes according to the present invention comprise an elongated hollow body that retains an electrically powered motor and drive mechanism that is used to drive one, two or more moveable bristle carriers. The elongated hollow body also includes an interior chamber for containing one or more batteries for powering the motor. And, one or more switches are provided along the outer region of the body for activating the motor and drive mechanism. As will be appreciated, a removable end cap is provided to enclose the interior chamber and provide a seal against external agents for the components inside the toothbrush body. As described in detail herein, the preferred embodiment toothbrushes comprise one, two or more movable bristle carriers. Each of the bristle carriers undergoes particular types of motion and the resulting combinations of movements provide unique cleaning efficacy.

As noted, the preferred embodiment electric toothbrushes comprise one or more bristle carriers that are driven by an electric motor and drive mechanism incorporated in the toothbrush. Preferably, these toothbrushes utilize two bristle carriers, each undergoing motion different than the motion of the other bristle carrier.

Figure 2:
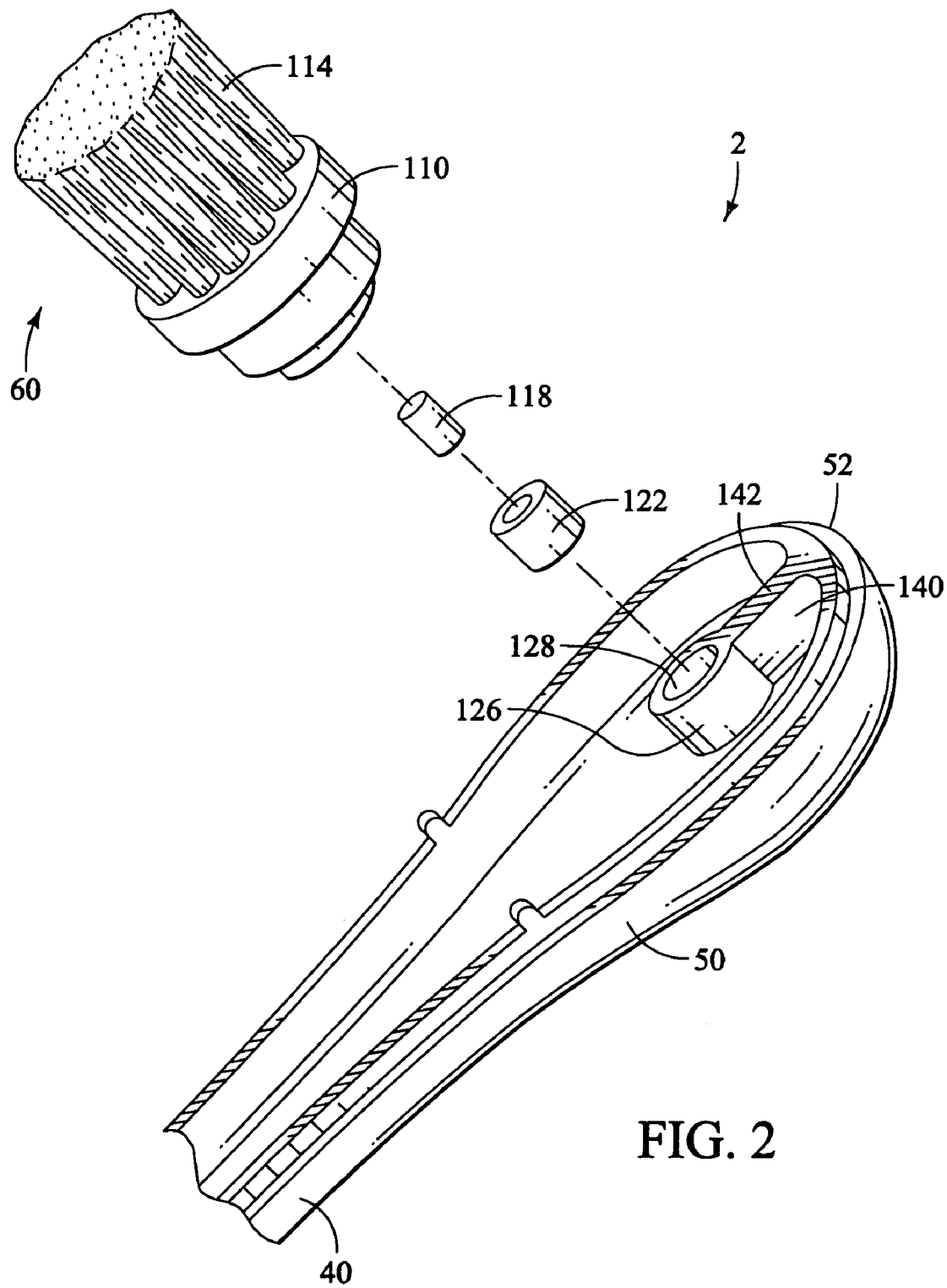
FIG. 2 is a partial exploded view of a head portion of a preferred embodiment toothbrush in accordance with the present invention.

FIG. 2 illustrates a preferred assembly configuration between a first bristle carrier 60 and the head and neck, i.e., 50 & 40 respectively, portions of the preferred embodiment toothbrush 2. The first bristle carrier 60 includes a base 110 having a plurality of bristles 114 extending outwardly therefrom. Defined within the interior portion of the head 50 is a sleeve receptacle 126. The sleeve receptacle 126 is preferably in the form of a cylindrical projection defining an interior mating surface 128. The mating surface 128 is adapted to receive a sleeve 122. The sleeve 122 in turn is sized to accommodate an axle 118 disposed within the interior of the sleeve 122. Extending between the sleeve receptacle 126 and the distal-most end 52 of the head portion 50 is preferably, a guide member or post 140. The guide member 140 defines a guide surface 142 described in greater detail herein.

Figure 3:
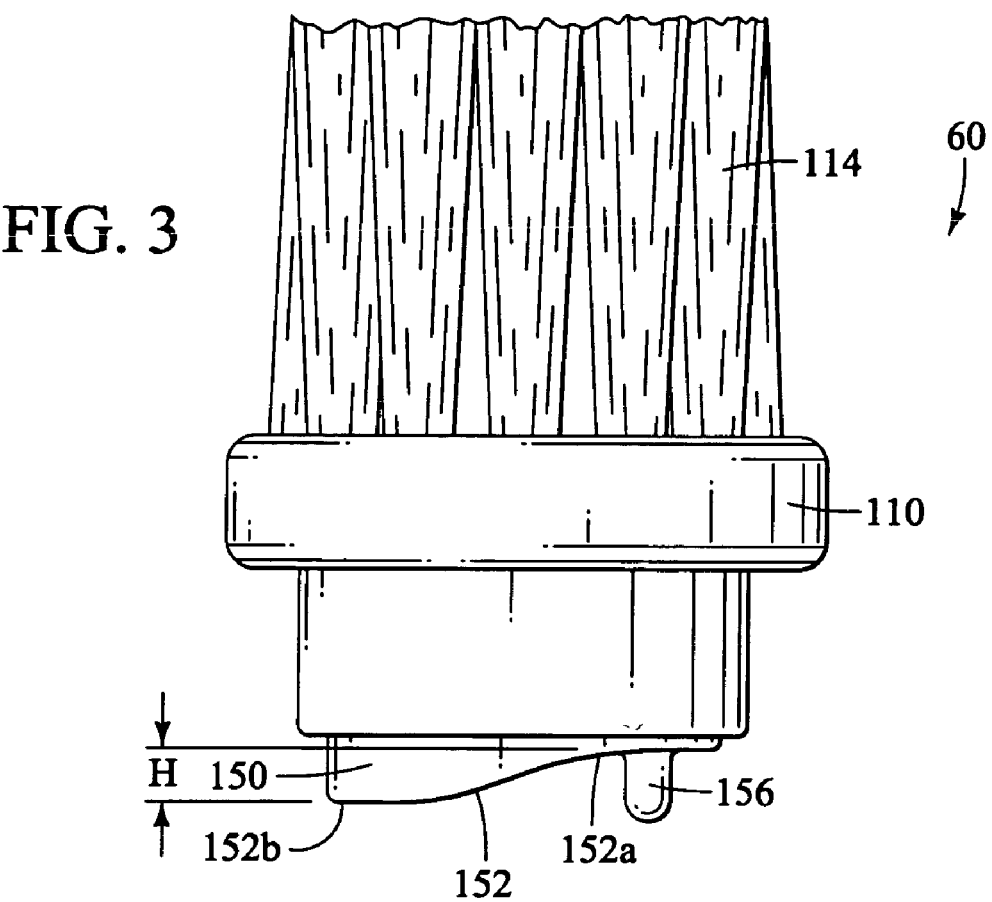
FIG. 3 is a side elevation view of a first bristle carrier utilized in the preferred embodiment toothbrush illustrated in FIG. 2.

FIG. 3 is a detailed side view of the first bristle carrier 60. Extending along the underside of the first bristle carrier base 110 is a first bristle carrier cam member 150. The cam member 150 defines a cammed surface or ramp 152 generally extending between a first location 152*a* and a second location 152*b* on the cam surface 152. Also extending from the underside of the first bristle carrier base 110 is an engagement member 156. The engagement member is adapted to attach to, or otherwise engage with, a drive shaft described in greater detail herein. The engagement member 156 may be in a variety of forms other than the cylindrical projection depicted in the figures. It is preferred that the drive shaft be directly coupled to the carrier, and most preferably by direct coupling to the engagement member. By "direct" coupling, it is meant that the shaft is coupled to the carrier during all phases or occurrences of motion of the drive shaft. The engagement member 156 may also serve as a stop member, also described in greater detail herein.

Figure 4:
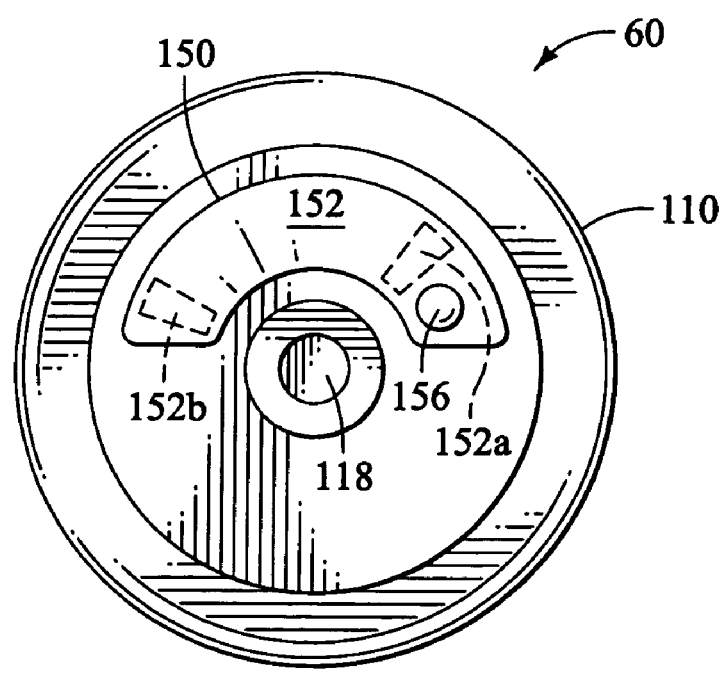
FIG. 4 is a view of the underside of the first bristle carrier shown in FIG. 3.

FIG. 4 illustrates the underside of the base 110 of the first bristle carrier 60. The cam member 150 is preferably in the form of an arcuate member extending about the center of the base 110 at which is located the axle 118. The first and second locations 152*a* and 152*b*, respectively, of the ramp surface 152 are shown in FIG. 4. Similarly it will be appreciated that the engagement member 156 is located adjacent the first location 152*a*.

Figure 5:
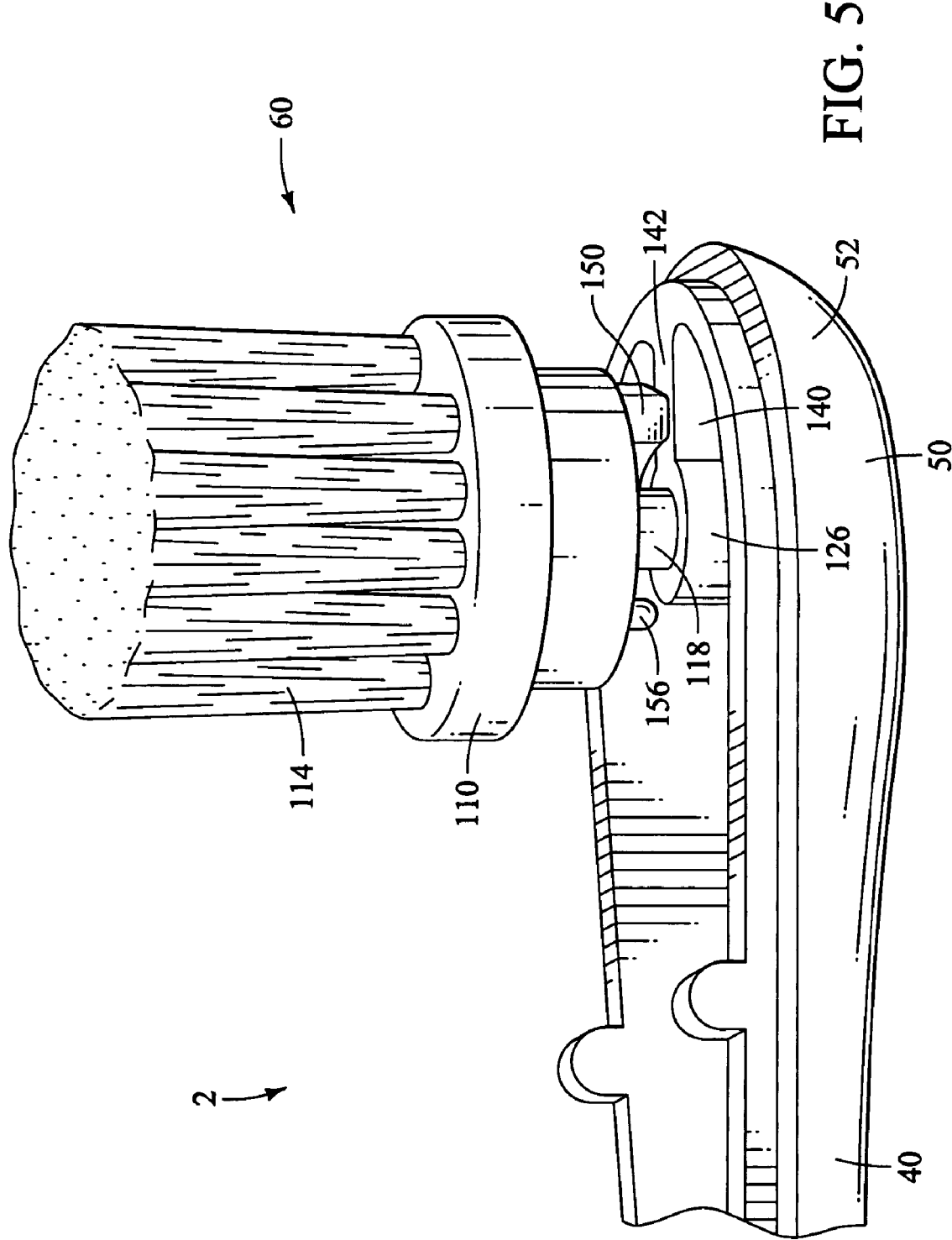
FIG. 5 is a perspective view of a partially assembled head portion of the preferred embodiment toothbrush.

FIG. 5 is a detailed perspective view of a partially exploded view of the head portion 50 and neck portion 40 of the preferred embodiment toothbrush 2. In this view, the first bristle carrier 60 is shown attached to and/or rotatably supported on the head 50 by axle 118 received within the receptacle 126. Furthermore, it will be noted that the cam member 150 is in engagement with the guide surface 142 of the guide member 140. Specifically, the cammed surface 152 (not shown) is in contact with the guide surface 142.

Figure 6:
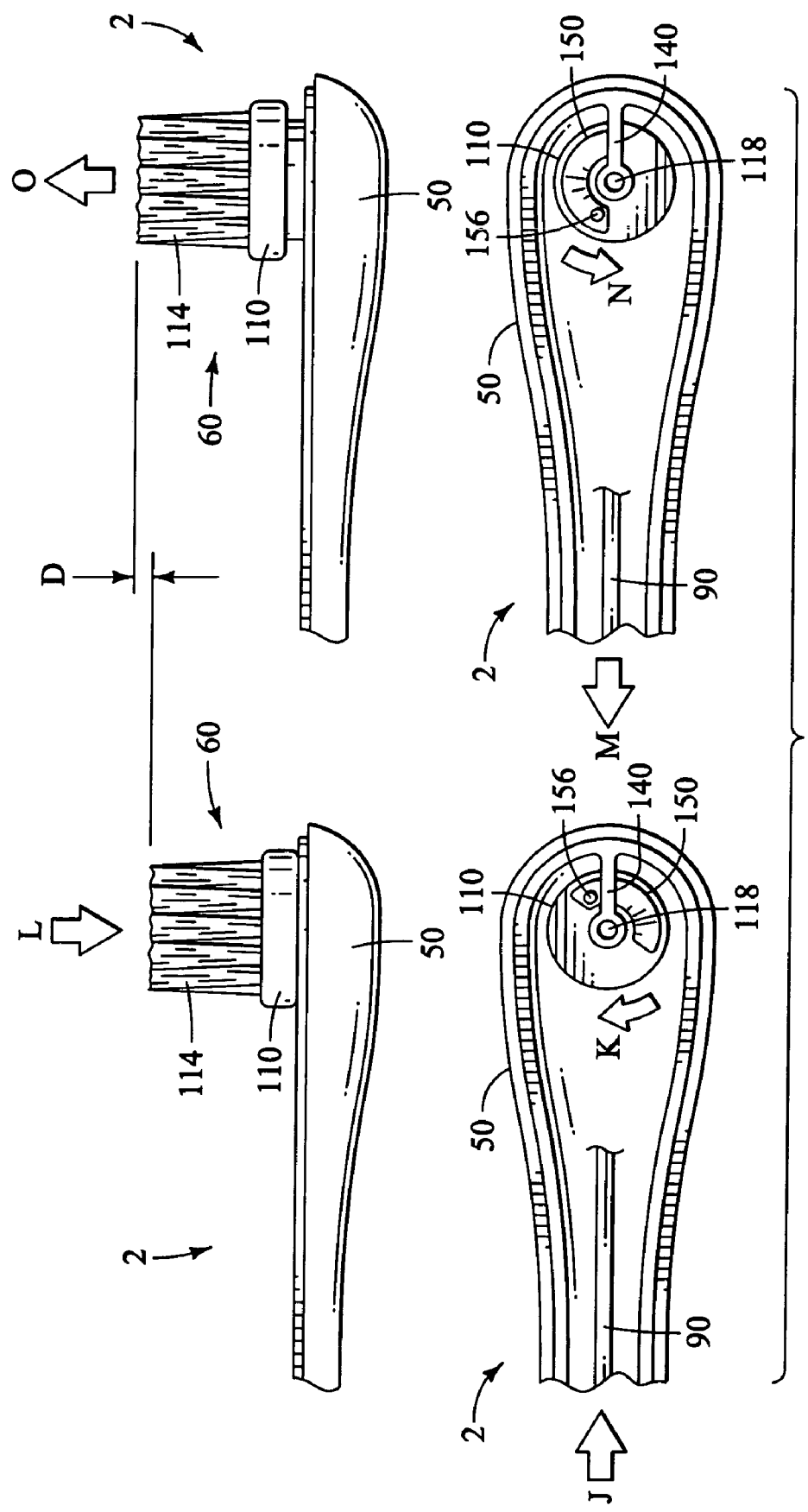
FIG. 6 is a collection of views of the head portion of the preferred embodiment toothbrush illustrating the displacement of the first bristle carrier during operation of the brush.

FIG. 6 illustrates the respective motions that the first bristle carrier 60 undergoes during operation of the preferred embodiment toothbrush 2. It will be appreciated that the top elevation side views correspond to the lower planar views of the brush head. It will be understood that the lower views of the brush head are schematic views and depict the underside of the carrier base 110, the cam member 150, and the guide member or post 140, as if the underside of the head 50 were transparent. The left-most views illustrate the toothbrush during a first phase during its operation, while the right-most views illustrate the position of the brush components during a second phase of operation of the toothbrush. Specifically, the preferred embodiment toothbrush 2 includes a drive shaft 90. The distal end of the drive shaft 90 is coupled to the engagement member 156. For clarity purposes, this coupling is not shown. Preferably, the drive shaft 90 undergoes a reciprocating motion during operation of the toothbrush 2. Upon movement of the drive shaft 90 in the direction of the arrow shown in the lower left diagram, i.e. in the direction of arrow J, the first bristle carrier base 110 is rotated in the direction of arrow K. This rotation about the center or axle 118 allows movement of the base 110 in the direction of arrow L shown in the upper left diagram. Upon movement of the drive shaft 90 in the direction of arrow M, shown in the lower right diagram, the base 110 is rotated in the direction of arrow N about the axle 118. This rotational motion urges the carrier 60 and specifically its base 110 outward from the head 50 in the direction of arrow O shown in the upper right diagram. The engagement member 156 may serve as a stop member to prevent over-rotation or excessive oscillation of the base 110 during operation. That is, the engagement member 156 can serve to ensure that the guide surface 142 remains in contact with the cam surface 152. Generally, after the carrier 60 has been displaced outward a distance D in the direction of arrow O, application of force to the brush head by the user during a brushing operation causes displacement and return of the carrier 60 in the direction of arrow L. The present invention encompasses embodiments in which a spring or other biasing member is utilized to return, or assist in returning, the carrier 60 to the brush head in the direction of arrow L.

Referring further to FIGS. 3 and 4, it will be appreciated that the configuration, shape, and size of the cam member 150 may vary depending upon the extent of pulsating motion desired, the frequency and stroke length of reciprocation of the drive shaft 90, and other factors. For example, the angle of inclination of the ramp surface 152, particularly between locations 152a and 152b may be a constant angle, or may be a varying angle with respect to plane X of the brush. It will be understood that if a varying angle or other nonlinear configuration is used for the ramp surface 152, the pulsating characteristics of the carrier 60 may readily be changed. Additionally, the difference in height between locations 152a and 152b, such as shown by dimension H depicted in FIG. 3, primarily determines the dimension D depicted in FIG. 6. Generally, this dimension may range from, as a lower limit, about 0.1 mm, more preferably about 0.5 mm, more preferably about 0.75 mm, more preferably about 1.0 mm, more preferably about 1.5 mm, to, as an upper limit, about 5.0 mm, more preferably about 4.0 mm, more preferably about 3.0 mm, and more preferably about 2.5 mm.

Figure 7:
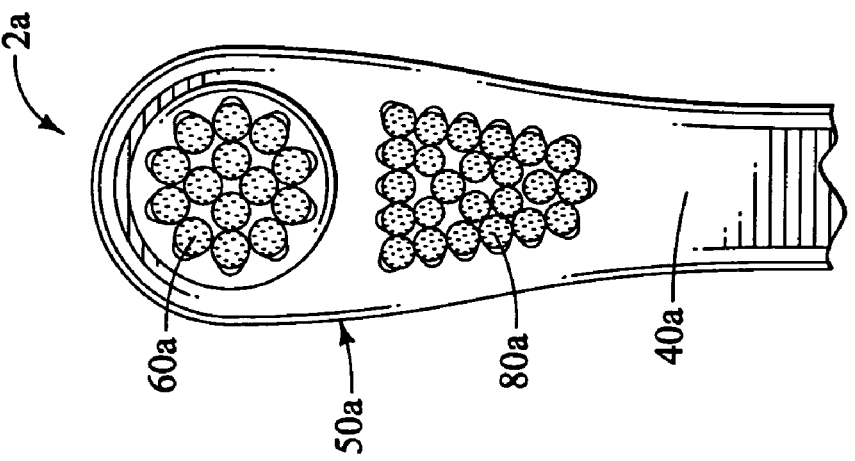
FIG. 7 is a front view of a head portion of another preferred embodiment toothbrush in accordance with the present invention.

The preferred embodiment toothbrush may utilize any number of a combination of bristle carriers in further combination with collections or arrays of static bristles. For example, FIG. 7 illustrates an embodiment of another preferred embodiment toothbrush 2a having a head 50a and a neck 40a. Disposed on the distal-most end of the head 50a is a first bristle carrier 60a. Disposed elsewhere on the head 50a are a plurality of static bristles 80a.

Figure 8:
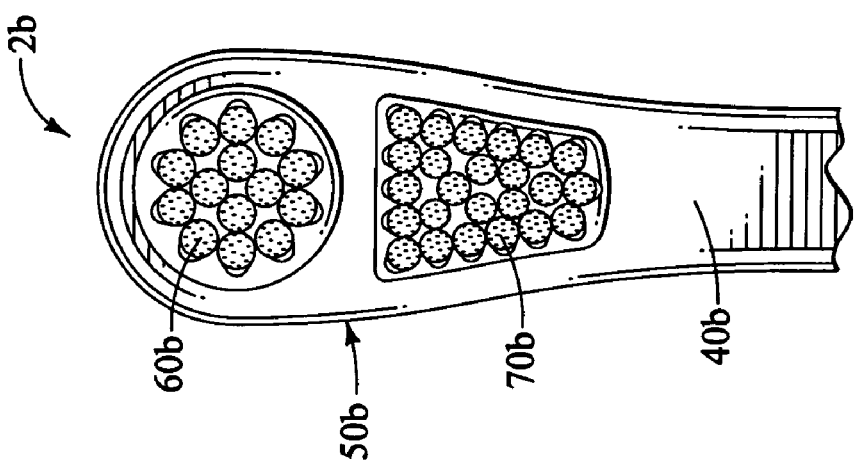
FIG. 8 is a front view of yet another preferred embodiment toothbrush in accordance with the present invention.

FIG. 8 illustrates another preferred embodiment toothbrush 2b according to the present invention. Toothbrush 2b comprises a head 50b and a neck 40b. Disposed on the head 50b is a first bristle carrier 60b and a second bristle carrier 70b.

Figure 9:
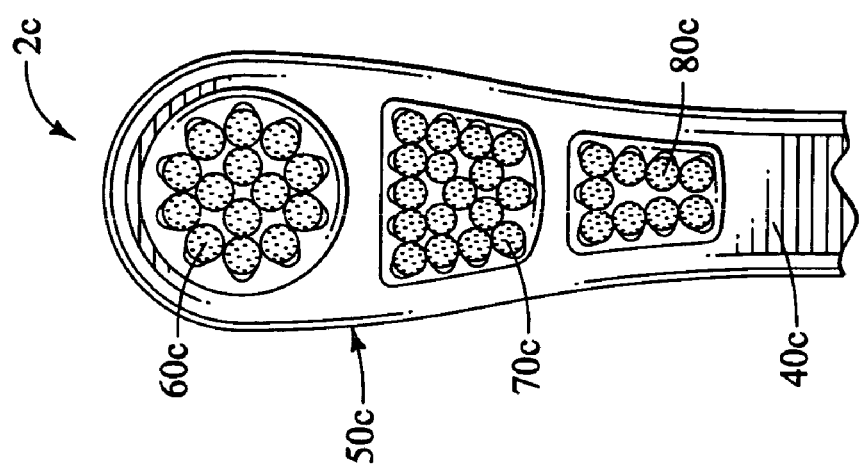
FIG. 9 is a front view of still another preferred embodiment toothbrush in accordance with the present invention.

FIG. 9 depicts another preferred embodiment toothbrush 2c. The toothbrush 2c includes a head 50c and a neck 40c. Disposed on the distal-most end of the head 50c is a first bristle carrier 60c. A second bristle carrier 70c is disposed alongside or proximate the first bristle carrier 60c. An array of static bristles 80c are located between the second bristle carrier 70c and the neck 40c.

In each of the embodiments depicted in FIGS. 7, 8, and 9, the first bristle carrier 60a, 60b, and 60c preferably undergoes the same combination of movements as described herein for the bristle carrier 60 of the toothbrush 2. That is, upon operation of the toothbrush 2a, 2b, or 2c, the carrier 60a, 60b, or 60c undergoes both an oscillating motion and a pulsating motion.

It will be appreciated that the second bristle carriers, such as for instance carriers 70b and 70c, or any of additional carriers such as a third or a fourth carrier, may undergo any type of motion. Preferably, it is contemplated that the second bristle carrier undergo a side-to-side motion, i.e. within plane X, and preferably that this motion be reciprocating motion. Alternatively, it is also preferred that the second bristle carrier undergo a reciprocating motion that is generally parallel with the longitudinal axis of the head and/or that of the handle of the toothbrush. The present invention also includes embodiments in which the second bristle carrier pulsates in a similar fashion as the first carrier. Furthermore, the present invention include embodiments in which the second carrier undergoes an oscillating and pulsating motion, while the first carrier and/or another carrier undergoes some type of motion. As previously noted, any of the carriers may undergo any type of motion such as angular motion, linear motion, curvilinear motion and variations of these motion types.

Figure 10:
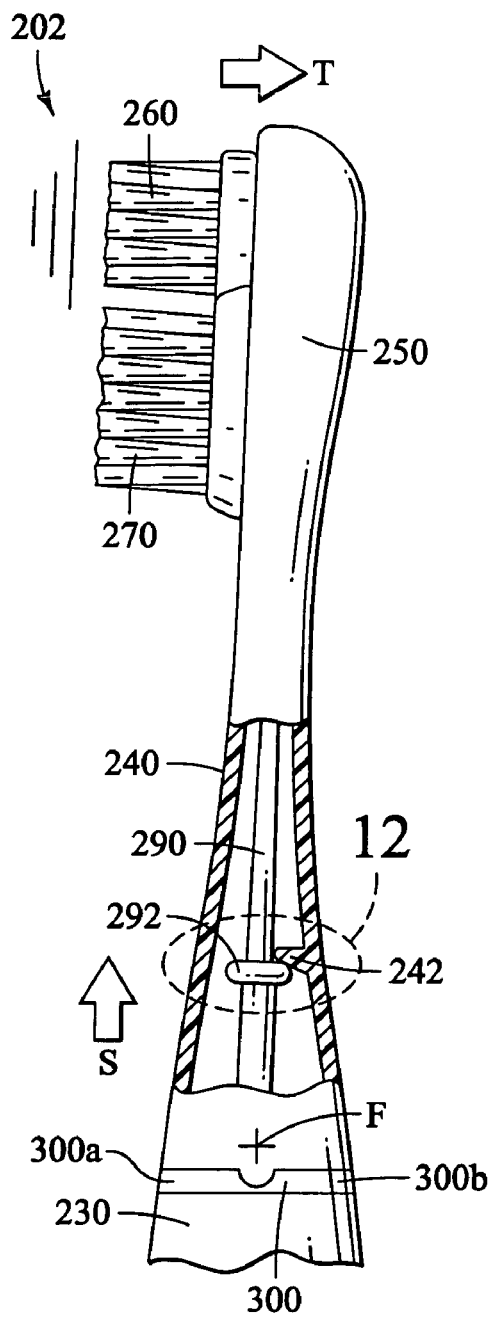
FIG. 10 is a partial fragmentary side view of a head portion of another preferred embodiment toothbrush during a first direction of travel of a reciprocating drive shaft in accordance with present invention.

The present invention toothbrush also includes embodiments in which motion is imparted to the entire head and/or at least a part of the neck portion of the toothbrush. This is in distinction to the previously described embodiments in which only one or more bristle carriers located on the head undergo motion during operation of the toothbrush. FIG. 10 illustrates such a preferred embodiment toothbrush 202 having a head 250, a handle 230, and a neck 240 extending therebetween. As described in greater detail herein, a flexible member 300 is preferably provided between the end or base of the neck 240 and the handle 230. Disposed on the head 250 is a first bristle carrier 260, and a second bristle carrier 270. A drive shaft 290 extends within the neck 240 and preferably undergoes a reciprocating motion during operation of the brush. Disposed along the exterior periphery of the drive shaft 290 is an engagement collar 292. The engagement collar 292 is located at a position on the drive shaft 290 such that during operation of the toothbrush and reciprocation of the drive shaft 290, the collar 292 periodically contacts, and preferably engages, a guide member 242. The guide member 242 is preferably formed such that it extends inwardly from the interior surface of the neck 240. FIG. 10 illustrates that during movement of the drive shaft 290 in the direction of arrow S, the collar 292 periodically contacts and engages the guide member 242. Due to the configuration of the guide member 242, described in greater detail herein, the neck 240 and head 250 are displaced in the direction of arrow T. More specifically, the displacement generally occurs in an angular or pivoting motion about point F.

Figure 11:
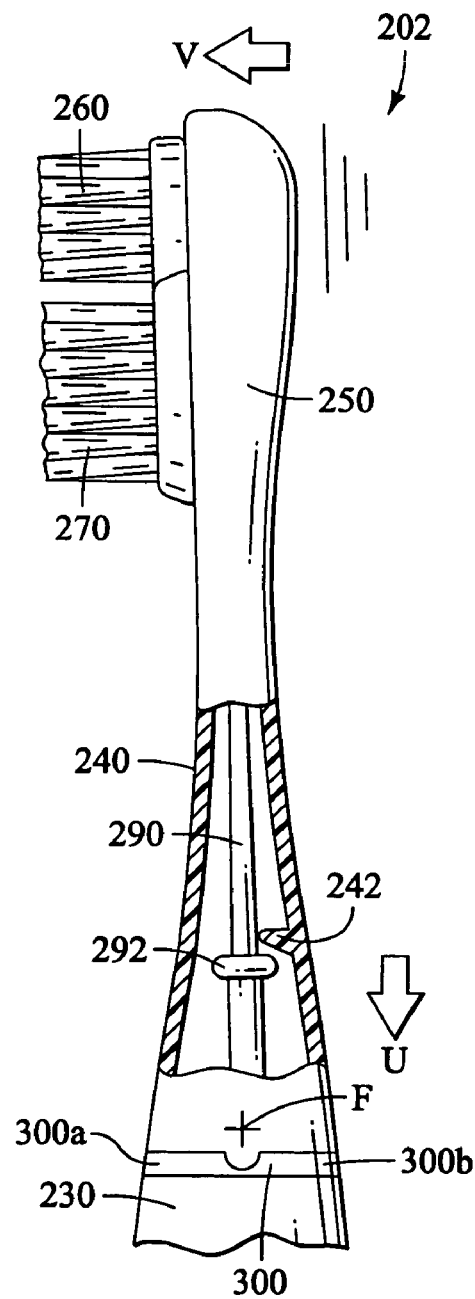
FIG. 11 is a partial fragmentary side view of the toothbrush depicted in FIG. 10 during a second direction of travel of the drive shaft.

FIG. 11 illustrates movement of the head 250 and the neck 240 during continued operation of the brush and movement of the drive shaft 290 in the direction of arrow U. This disengagement between the collar 292 and the guide member 242 results in the head moving in an opposite direction such as shown in the direction of arrow V in FIG. 11.

Figure 12:
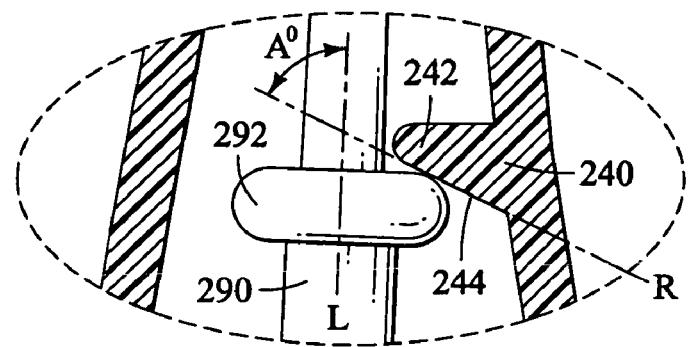
FIG. 12 is a detailed partial cross-sectional view illustrating the engagement between the drive shaft and a guide member utilized in the toothbrush depicted in FIG. 10.

FIG. 12 is a detailed partial cross-sectional view of the relationship between the collar 292 of the drive shaft 290 and the guide member 242 extending from the interior surface of the neck 240. Preferably, the guide member 242 defines a guide surface 244. It is this guide surface 244 that contacts a portion of the collar 292 and causes displacement of the neck 240 during movement of the drive shaft 290 along the longitudinal axis L. The guide surface 244 preferably extends at some angle with respect to the longitudinal axis L of the drive shaft 290. This angle is designated as angle A as shown in FIG. 12. Angle A may be any angle of the guide surface 244 that, as a result of periodic engagement with the collar 292 during reciprocation of the drive shaft 290, imparts movement to the head of the toothbrush. Generally, as a lower limit, angle A is from about 5°, more preferably about 10°, more preferably about 20°, more preferably about 30°, and more preferably about 40°. As an upper limit, angle A is to about 85°, more preferably to about 80°, more preferably to about 70°, more preferably to about 60°, and more preferably to about 50°.

It will be appreciated that instead of the collar 292 being a separate component from the drive shaft 290 and so, must be assembled or affixed thereon, the collar 292 could be integrally formed with the drive shaft 290.

Figure 13:
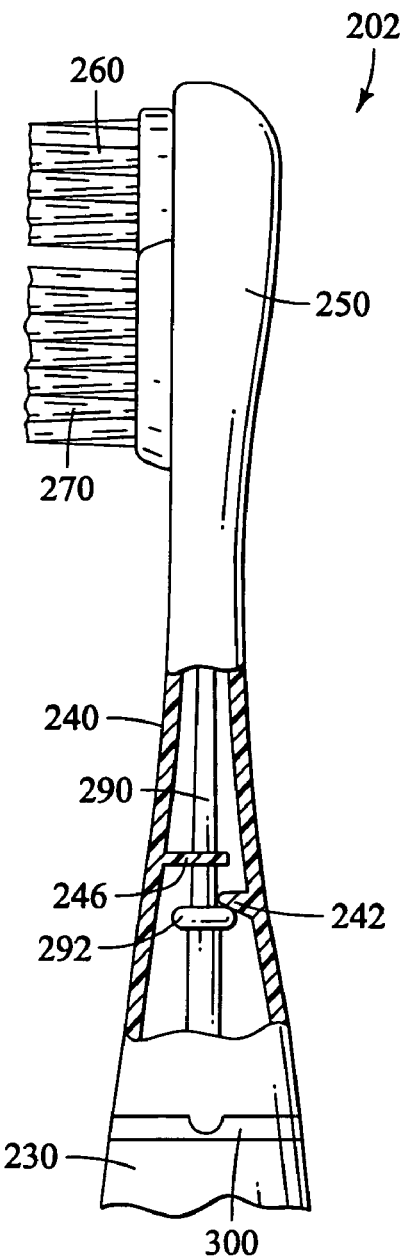
FIG. 13 is a partial fragmentary side view of the toothbrush shown in FIGS. 10 & 11 having a secondary stabilizing member provided.

FIG. 13 illustrates a variant configuration of the preferred embodiment toothbrush 202. In this alternate version, a second member 246 is provided within the interior of the neck portion 240. This secondary member 246 provides assistance and promotes alignment of the drive shaft 290 during reciprocation of the drive shaft 290.

The preferred embodiment toothbrushes may also utilize a drive mechanism in which the drive shaft 290 undergoes an orbital type motion rather than reciprocation. For example, as shown in FIGS. 14 & 15, the drive shaft 290, while undergoing orbital motion, rotates about a center point C shown in FIG. 15 generally along path P. Referring to FIG. 14, it will be seen that as the drive shaft 290 rotates in this matter it periodically contacts and preferably engages a first orbital guide member 245 extending from the interior of the neck 240. This contact and engagement displaces the neck portion and head portion as previously described. As the drive shaft 290 continues along its path P and disengages from the member 245, the head portion and the neck portion return to their previous positions. In a preferred aspect, the drive shaft 290 undergoes a single motion. That is, as the drive shaft 290 undergoes orbital motion about the center point C, the shaft 290 is not undergoing any other motion such as a linear displacement of either or both of its ends, or any deviation from the circular paths resulting from orbital motion.

Yet another alternate version is depicted in FIG. 16. In this alternate version, a plurality of guide members are provided such as the first orbital guide member 245 and a second orbital guide member 247.

Referring further to FIGS. 10 and 11, it will be appreciated that a first direction of travel of the brush head 250 is primarily due to engagement between the drive shaft 290 or rather its collar 292, and the guide member 242. The second direction of travel, i.e. generally in the opposite direction as that of the first direction, is primarily due to release of prior loading of the flexible member 300. This characteristic is referred to herein as a bias return. During the first direction of travel of the head 250 and neck 240, such as in the direction of arrow T shown in FIG. 10, the region 300b of the member 300 is compressed and the opposite region 300a of the member 300 is placed under tension. During the second direction of travel of the brush head 250 and neck 240, such as in the direction of arrow V shown in FIG. 11, the head 250 and neck 240 move as the flexible member 300 returns to its previous configuration. The stiffness, resilience, and degree and ease (or resistance) of deformation of the flexible member 300 may be selected as desired. Furthermore, it is contemplated that one or more regions of the member 300 such as regions 300a and/or 300b, may be provided with different physical characteristics to provide desired aspects of motion during operation of the toothbrush.

The previous description is generally for a neck configuration utilizing a single interior guide member 242. Preferably, the guide member 242 is provided within the desired plane of motion within which the head 250 and neck 240 move. For example, if it is desired for the head and neck to pivot or move generally within the Y plane of the brush then the guide member 242 should be located along an interior region of the neck 240 as shown in FIGS. 10 and 11, at a region of the neck which is either located nearest the user or farthest from the user during operation of the toothbrush.

The toothbrush embodiment depicted in FIG. 16 which utilizes two guide members 245 and 247, can eliminate the need for a flexible member that provides a bias return for the head and neck.

Moreover, a bias return can be provided in a toothbrush without the presence of a flexible member 300. Instead, the bias return can be provided by the materials of construction of the neck 240 and/or head 250.

As with the alternate embodiments shown in FIGS. 7-9 utilizing various combinations and numbers of bristle carriers and optionally in conjunction with bristles extending from the head and/or neck regions (referred to as static bristles), the toothbrushes depicted in FIGS. 10-16 may also utilize various combinations and various numbers of bristle carriers. Moreover, the toothbrushes of FIGS. 10-16 may also utilize bristles that extend directly from the head and/or neck regions. Such bristles would not be "static" as that term is used herein since upon operation of the toothbrush and movement of the head and neck, the bristles are placed in motion. However, the bristles could still be considered as "static" relative to the head and neck.

While the embodiments of the present invention have been illustrated for simplicity with bristles which extend in a direction substantially perpendicular to the longitudinal axis and the surface of the bristle carriers, it is contemplated that the bristles might be arranged differently to complement or further enhance the motions of the first and/or second bristle carriers. That is, some or all of the bristles might extend in a direction which forms an acute angle to a surface of the bristle carrier and extend in a direction toward or away from the handle. In another embodiment, some of the bristles might extend outwardly away from the head, in another direction, again forming an acute angle with respect to the surface of the bristle carrier. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910; the substances of which are incorporated herein by reference.

A variety of drive mechanisms may be utilized in the preferred embodiment toothbrushes described herein. As noted, drive mechanisms that provide a powered reciprocating or orbiting output are preferred. For example, U.S. Pat. Nos. 5,617,603; 5,850,603; 5,974,615; 6,032,313; 5,504,959; 5,524,312; 5,625,916; 5,732,432; 5,070,567; 5,170,525; 5,416,942; 3,588,936; 5,867,856; and 4,397,055, the substances of which are incorporated herein by reference, disclose other motor and rotating or oscillating shaft arrangements that might be suitable. Furthermore, the drive mechanisms disclosed in U.S. Ser. No. 10/027,594, filed Dec. 21, 2001, now abandoned; and U.S. Ser. No. 09/993,167, filed Nov. 6, 2001, now U.S. Pat. No. 6,725,490, both of which are incorporated herein by reference, may be used. Additionally, any or all of the aspects of U.S. Pat. Nos. 5,617,601 and 5,435,032, both of which are hereby incorporated herein, may be utilized in the toothbrushes described herein.

Another preferred mechanism for imparting motion to one or more bristle carriers is described in provisional application Ser. No. 60/361,625, filed Mar. 4, 2002, herein incorporated by reference. That mechanism imparts a "side-to-side" motion to a bristle carrier. Referring to FIG. 1, such motion causes either of both of the bristle carriers 60 and 70 to reciprocate within the plane of the toothbrush head, e.g. within the X plane, or within a plane parallel thereto, and in a direction generally perpendicular to the longitudinal axis of the toothbrush.

A variety of different mechanisms may be used to provide the noted motions described herein. These mechanisms may utilize either a rotating or oscillating shaft or a linearly reciprocating shaft as a power source. Generally, the various repeating periodic motions are achieved by arrangements of pivoting members and linkage assemblies that have certain predetermined regions of freedom. Accordingly, rotating or reciprocating motion from a powered shaft may be translated to a linear, primarily linear, curvilinear, or a three dimensional motion by particular selection and configuration of components forming the drive mechanism. Furthermore, guide channels may be provided along or within the head or region of the toothbrush body near the bristle carrier(s) for assisting or guiding the movement of the bristle carrier(s).

Additionally, it will be appreciated that any of the mechanisms or drive trains described or illustrated herein may be combined with any of the other mechanisms or drive trains noted herein. And, portions of any of these mechanisms may be combined with portions of any other mechanism noted herein. It is also contemplated that a toothbrush as described herein may employ two of the drive trains noted herein, such that each drive train powers a particular bristle carrier. Accordingly, two electrical motors could also be utilized, one for each drive train.

Furthermore, it is contemplated that a toothbrush embodiment can utilize both the features of the toothbrush depicted in FIGS. 1-9 and also the features of the toothbrush depicted in FIGS. 10-16. For example, a toothbrush can be provided with a flexible member 300, a guide member 242, and a reciprocating drive shaft 290 that induces motion to the entire head and neck assembly, in conjunction with a bristle carrier 60 having a cam member 150 and post 140 that induces pulsating motion and/or an oscillating motion of the carrier 60 with respect to the head.

Selection of materials for the various components in the toothbrushes of the present invention is an important consideration. The toothbrushes employ various inclined ramps or cam surfaces to impart particular motions to one or more bristle carriers. Accordingly, the durability and wear resistance of those components and their respective surfaces are desirably promoted by the proper selection of materials. These components may be formed from a wide array of materials. Generally, it is preferred that these components exhibit low friction characteristics. Other components utilized in the toothbrushes described herein serve as bearings or points for supporting a rotating element. These components are preferably formed from low friction materials, or even materials having an internal lubricity.

It is further contemplated in certain applications to provide access openings or apertures in the head or neck region so that water in the environment from a typical brushing operation, may enter the interior of the brush head and serve to lubricate the various external surfaces of the various components.

Additionally, in the toothbrushes described in FIGS. 10-16, the flexible member 300 may be made from a variety of materials. Generally, these materials are flexible and exhibit a limited degree or resistance to deformation. Upon being deformed, i.e. a load being placed thereon, and then the load being removed, the material should readily return to its previous shape and configuration. An indication as to the desired compressive, stiffness, and/or resilience characteristics of the material used for the flexible member is as follows. For an electric toothbrush of typical dimensions, it is preferred that the flexible material have a thickness and characteristics such that a brushing load of from about 1 to about 3 pounds can be placed upon the brush head without fully compressing the flexible member. That is, it is desired that upon such a load being placed upon the brush head, the flexible member retain an adequate amount of reserve or capacity for further additional loading, and that such loading, i.e. from about 1 to 3 pounds, not cause permanent deformation of the flexible member upon release of the load.

It is contemplated that a wide array of materials and/or combinations of materials could be utilized for the flexible member. For example, various foamed materials or other cellular matrix could be employed. A viscoelastic foam or matrix could be used having time-dependent properties. A bonded foam could be used in which two or more different foams are adhered together. Moreover, instead of or in addition to foams, viscoelastic fluids which are generally incompressible could be used. A flexible member formed from an incompressible material would therefore not compress, but instead undergo some type of displacement. Additionally, the flexible member could utilize one or more regions of segmentation, each region having separate and distinct properties. It is further contemplated that the flexible member utilize one or more covering materials that may serve to protect the underlying material, or to assist in stiffness, resilience, or deformation characteristics of the flexible member.

The head and neck portions of the preferred embodiment toothbrushes described herein can be formed from an array of polymeric materials. In the following description of the preferred polymer materials for use herein, the abbreviations that are commonly used by those of skill in the art to refer to certain polymers appear in parentheses following the full names of the polymers. An example of a preferred polymer is polypropylene ("PP"), or may be selected from the group consisting of other conventional toothbrush materials, such as polystyrene ("PS"), polyethylene ("PE"), acrylonitrile-styrene copolymer ("SAN"), and cellulose acetate propionate ("CAP"). Another exemplary polymer is preferably a thermoplastic elastomer ("TPE"), a thermoplastic olefin ("TPO"), a soft thermoplastic polyolefin (e.g., polybutylene), or may be selected from other elastomeric materials, such as ethylene-vinylacetate copolymer ("EVA"), and ethylene propylene rubber ("EPR"). Examples of suitable thermoplastic elastomers herein include styrene-ethylene-butadiene-styrene ("SEBS"), styrene-butadiene-styrene ("SBS"), and styrene-isoprene-styrene ("SIS"). Examples of suitable thermoplastic olefins herein include polybutylene ("PB"), and polyethylene ("PE"). A particularly preferred polymeric material for use in forming the head and/or neck, is a commercially available material under the designation Celcon®.

In addition, color can be provided to give the neck and head portions of the toothbrush an aesthetically pleasing appearance. Opaque or translucent colors can be provided. For translucent brushes an insert can further be provided in the neck and/or head. Such inserts can be any color and are typically made from a polypropylene material.

Techniques known to those of skill in the art, such as injection molding, can be used to manufacture the head and neck components. Any design, shape, or configuration for the handle and/or the bristles is suitable herein.

The flexible neck can also act to buffer excessive force on the teeth and gums that may be exerted by a user. Application of excessive force during brushing is deleterious to the gums. Accordingly, by appropriate selection of the materials forming the neck of the preferred embodiment toothbrush described herein, application of excessive force can be prevented.

Additional aspects and details of preferred toothbrush components, manufacture, and use are described in U.S. application Ser. Nos. 60/410,864; 60/410,556; 60/410,865; 60/387,841; 10/128,018 now abandoned; Nos. 60/419,672; 60/410,902; 60/410,903; 60/410,853; 60/464,787; 60/487,670; all of which are hereby incorporated by reference.

The present invention has been described with reference to particular embodiments. Modifications and alternative forms will occur to others upon reading and understanding this specification. Furthermore, it is contemplated that any of the features or aspects of any of the toothbrushes described herein may be combined with or utilized in conjunction with any of the other features or aspects of any of the toothbrushes described herein. It is tended that all such modifications and alternations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
   an elongate handle having a motor disposed therein;
   a head having a longitudinal axis and a movable bristle carrier disposed thereon, wherein said head is stationary during use;
   a neck extending between said handle and said head;
   a shaft directly coupled to said movable bristle carrier and operatively connected to said motor;
   wherein movement of said shaft causes said movable bristle carrier to oscillate about an axis generally perpendicular to said longitudinal axis of said head and to reciprocate along said axis generally perpendicular to said longitudinal axis of said head and wherein said movable bristle carrier further comprises a ramp disposed on an underside surface thereof and said head further comprises a post, wherein said ramp and said post are slidingly engaged, wherein said movable bristle carrier further comprises a stop member at one end of said ramp, and wherein said stop member is in the form of a pin extending from an underside of said movable bristle carrier.

2. The electric toothbrush of claim 1, further comprising a second movable bristle carrier disposed between said movable bristle carrier and said handle.

3. The electric toothbrush of claim 2, wherein said second movable bristle carrier reciprocates along said longitudinal axis of said head.

4. The electric toothbrush of claim 1, wherein said shaft reciprocates.

* * * * *

UNITED STATES PATENT AND TRADEMARK OFFICE
CERTIFICATE OF CORRECTION

| | | |
|---|---|---|
| PATENT NO. | : 7,698,771 B2 | Page 1 of 1 |
| APPLICATION NO. | : 11/015111 | |
| DATED | : April 20, 2010 | |
| INVENTOR(S) | : Douglas A. Gall et al. | |

It is certified that error appears in the above-identified patent and that said Letters Patent is hereby corrected as shown below:

Title page
    (75) Inventor: Please delete "Douglas A. Gall, Strongsville, OH (US)" and insert -- Douglas A. Gall, Strongsville, OH (US) and John Geoffrey Chan, Loveland, OH (US) --.

Signed and Sealed this

Thirteenth Day of July, 2010

David J. Kappos
*Director of the United States Patent and Trademark Office*